US008656765B2

(12) United States Patent
Kita et al.

(10) Patent No.: US 8,656,765 B2
(45) Date of Patent: Feb. 25, 2014

(54) FUEL PROPERTY DETECTION DEVICE FOR CONSTRUCTION MACHINE AND CONSTRUCTION MACHINE PROVIDED THEREWITH

(75) Inventors: Tomotaka Kita, Hiroshima (JP); Yoshihiko Ueda, Hiroshima (JP)

(73) Assignee: Kobelco Construction Machinery Co., Ltd., Hiroshima-shi (JP)

( * ) Notice: Subject to any disclaimer, the term of this patent is extended or adjusted under 35 U.S.C. 154(b) by 15 days.

(21) Appl. No.: 13/505,147

(22) PCT Filed: Oct. 7, 2010

(86) PCT No.: PCT/JP2010/006014
§ 371 (c)(1),
(2), (4) Date: Apr. 30, 2012

(87) PCT Pub. No.: WO2011/052139
PCT Pub. Date: May 5, 2011

(65) Prior Publication Data
US 2012/0222473 A1    Sep. 6, 2012

(30) Foreign Application Priority Data
Oct. 30, 2009  (JP) .................................. 2009-250034

(51) Int. Cl.
*G01M 15/04* (2006.01)
(52) U.S. Cl.
USPC ...................................................... 73/114.38
(58) Field of Classification Search
USPC ........................................ 73/114.38, 114.55
See application file for complete search history.

(56) References Cited

U.S. PATENT DOCUMENTS

| 4,770,129 A | * | 9/1988 | Miyata et al. ................. 123/1 A |
| 4,945,880 A | * | 8/1990 | Gonze et al. .................. 123/674 |
| 4,945,885 A | * | 8/1990 | Gonze et al. .................. 123/520 |
| 5,060,619 A | * | 10/1991 | Sakurai et al. ............... 123/494 |
| 5,103,184 A | * | 4/1992 | Kapsokavathis et al. ..... 324/672 |
| 5,124,654 A | * | 6/1992 | Scheid ........................ 324/658 |
| 5,231,358 A | * | 7/1993 | Kapsokavathis et al. ..... 324/672 |
| 5,261,270 A | * | 11/1993 | Gonze et al. ................. 73/61.43 |

(Continued)

FOREIGN PATENT DOCUMENTS

| JP | 08 145966 | 6/1996 |
| JP | 09 043207 | 2/1997 |

(Continued)

OTHER PUBLICATIONS

International Search Report issued on Nov. 22, 2010 in PCT/JP10/006014 filed on Oct. 7, 2010.

*Primary Examiner* — Freddie Kirkland, III
(74) *Attorney, Agent, or Firm* — Oblon, Spivak, McClelland, Maier & Neustadt, L.L.P.

(57) ABSTRACT

A device detecting a property of fuel in a course of a pipeline, while improving accuracy and stability of the fuel property detection. The device includes a sub-tank provided in the course of a fuel pipeline connecting a fuel tank and an engine, and a sensor capable of detecting the property of fuel inside the sub-tank. The sub-tank includes a fuel inlet for introducing therethrough fuel from the fuel tank, and a fuel outlet for sending out therethrough the fuel toward the engine.

9 Claims, 10 Drawing Sheets

(56) References Cited

U.S. PATENT DOCUMENTS

| | | | |
|---|---|---|---|
| 5,945,831 A * | 8/1999 | Sargent et al. | 324/686 |
| 7,800,379 B2 * | 9/2010 | Hernandez et al. | 324/663 |
| 8,072,604 B2 | 12/2011 | Arakawa et al. | |
| 8,082,773 B2 * | 12/2011 | Nakamura et al. | 73/114.43 |
| 2009/0153149 A1 * | 6/2009 | Hernandez et al. | 324/663 |
| 2012/0260731 A1 * | 10/2012 | Austerlitz et al. | 73/32 R |

FOREIGN PATENT DOCUMENTS

| | | |
|---|---|---|
| JP | 11 013568 | 1/1999 |
| JP | 2008 014741 | 1/2008 |
| JP | 2008 261812 | 10/2008 |
| JP | 2008 267147 | 11/2008 |
| JP | 2009 229129 | 10/2009 |

* cited by examiner

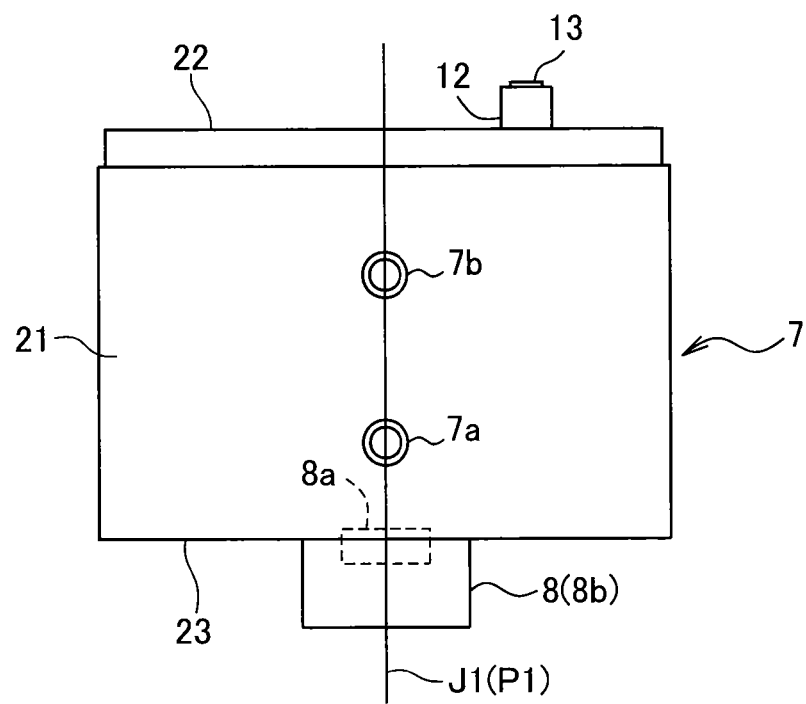

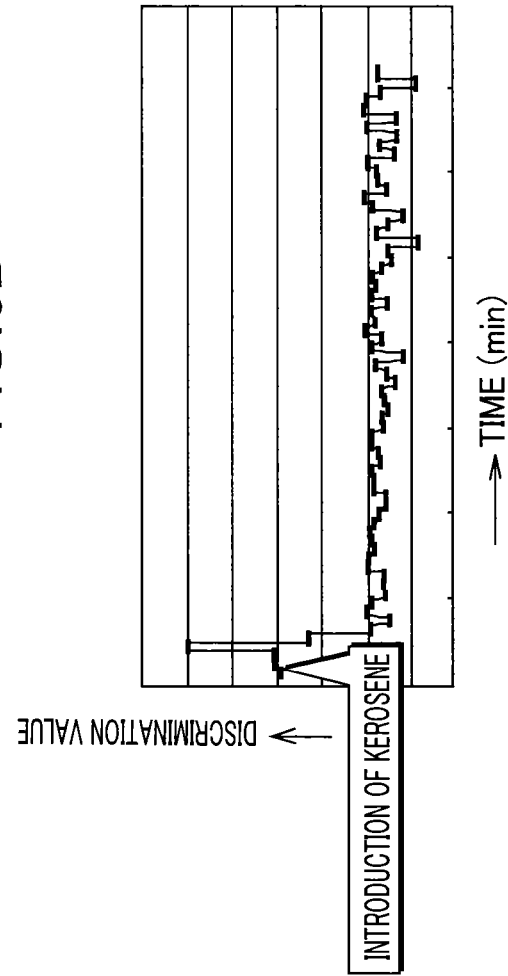
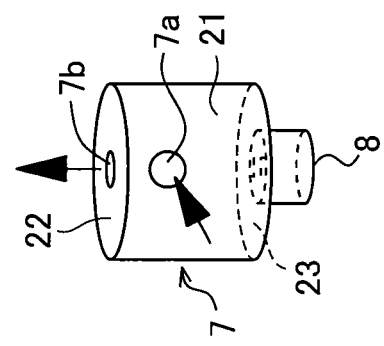
FIG.6A
FIG.6B

FUEL PROPERTY DETECTION DEVICE FOR CONSTRUCTION MACHINE AND CONSTRUCTION MACHINE PROVIDED THEREWITH

TECHNICAL FIELD

The present invention relates to a fuel property detection device provided in a construction machine, such as a hydraulic shovel, to detect a fuel property in order to determine adequacy of fuel to be supplied to an engine.

BACKGROUND ART

In the field of construction machines such as a hydraulic shovel, in order to prevent engine trouble, undesirable exhaust emissions and others due to the use of inadequate fuel, there has been known a device for detecting a property (physical property such as kinetic viscosity or density, or chemical property) of fuel to be supplied to an engine.

For example, the following Patent Document 1 discloses a device comprising a fuel tank for storing fuel, and a density sensor provided at a bottom of the fuel tank, in adjacent relation to an inlet of a suction pipe of the fuel tank, wherein the density sensor is operable to detect a density of fuel to be sucked into the suction pipe (conventional technique 1).

The Patent Document 2 discloses a device comprising: a small chamber which is defined in an upper region of an internal space of a fuel tank at a position facing a fuel filler opening, and formed with an inlet and an outlet; and a sensor capable of detecting a property of a part of fed fuel which stagnates in a bottom region of the small chamber (conventional technique 2).

However, in each of the conventional techniques 1 and 2, the sensor and associated structure are installed to the fuel tank itself. Thus, each of the conventional techniques 1 and 2 cannot be added on (added as an aftermarket option) to an existing construction machine, unless a fuel tank therein is subjected to significant modification or replacement.

Moreover, in the conventional technique 1, the sensor and associated structure protrude from a bottom surface of the fuel tank to the outside. Thus, due to a fuel tank installation space, interference with other devices, etc., layout flexibility during mounting on a construction machine will be deteriorated.

As a solution to such a problem, it is conceivable to detect a fuel property in the course of a fuel supply pipeline connecting a fuel tank and an engine, by a sensor provided in the course of the fuel supply pipeline (hereinafter referred to as "in-pipeline detection system").

Based on employing the in-pipeline detection system, it becomes possible to add on the sensor and associated structure to a construction machine without carrying out modification or replacement of a fuel tank itself. Moreover layout flexibility for mounting the sensor and associated structure to the construction machine is high.

However, in the in-pipeline detection system, it is necessary to detect a property of fuel which is flowing through the pipeline at a high flow velocity. Thus, due to difficulty in ensuring a time required for the fuel property detection, and a large variation in flow velocity and flow quantity of fuel, accuracy and stability of the detection becomes deteriorated.

LIST OF PRIOR ART DOCUMENTS

Patent Documents

Patent Document 1: JP 2008-261812 A
Patent Document 2: JP 2008-14741 A

SUMMARY OF THE INVENTION

It is an object of the present invention to provide a fuel property detection device capable of employing the in-pipeline detection system while improving accuracy and stability of the fuel property detection, and a construction machine equipped with the fuel property detection device.

The present invention provides a fuel property detection device for detecting a property of fuel to be supplied to an engine from a fuel tank for storing fuel. The fuel property detection device comprises: a sub-tank provided in the course of a fuel supply pipeline connecting the engine and the fuel tank, and capable of storing a specific amount of fuel; and a sensor provided to the sub-tank and capable of detecting the property of fuel within the sub-tank, wherein the sub-tank has a fuel inlet for introducing therethrough fuel from the fuel tank, and a fuel outlet for sending out therethrough the fuel toward the engine.

The present invention further provides a construction machine which comprises: the above fuel property detection device; a fuel tank connected to the inlet pipe of the fuel property detection device; and an engine connected to the outlet pipe of the fuel property detection device.

BRIEF DESCRIPTION OF THE DRAWINGS

FIG. 4 is a side view of the sub-tank illustrated in FIG. 1.

FIG. 6A is a diagram schematically illustrating a detection device according to a second embodiment of the present invention, and FIG. 6B is a graph illustrating a detection performance test result of the detection device.

DESCRIPTION OF EMBODIMENTS

With reference to the accompanying drawings, embodiments of the present invention will now be described. It should be noted that the following embodiments are specific examples of the present invention but not intended to limit the technical scope of the present invention.

(First Embodiment [Refer to FIGS. 1 to 5])

Figure 1:
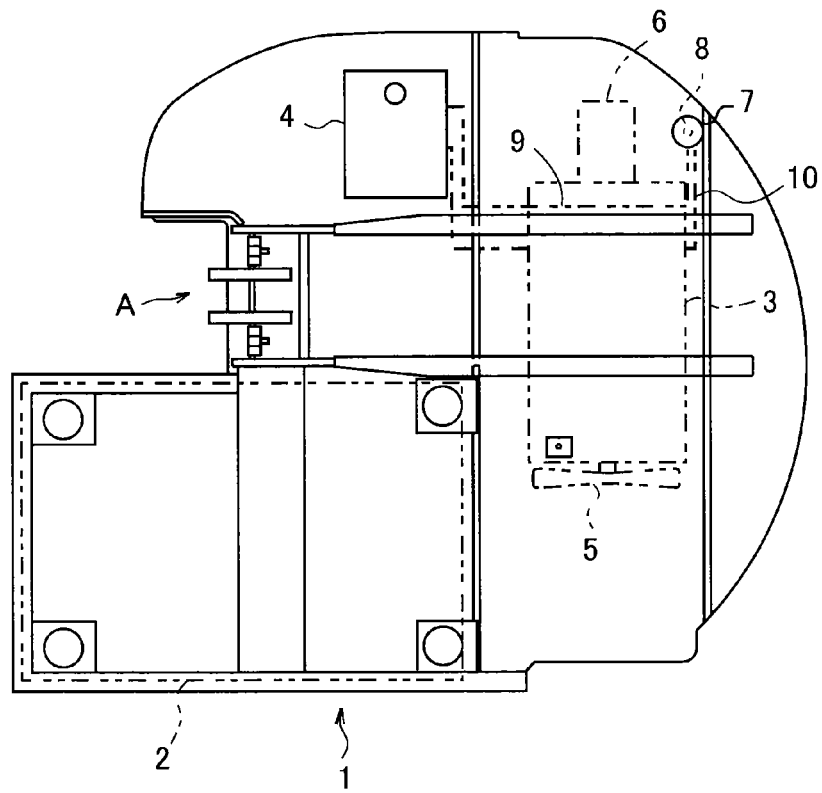
FIG. 1 is a schematic top plan view of an upper frame of a hydraulic shovel equipped with a detection device according to a first embodiment of the present invention.

FIG. 1 is a schematic top plan view of an upper frame of a hydraulic shovel equipped with a detection device according to a first embodiment of the present invention. The following description will be made using front-rear and right-left directions as viewed from an operator seated in a seat in a cabin 2 (the left direction in FIG. 1 corresponds to a front direction, and the up direction in FIG. 1 corresponds to a right direction).

As illustrated in FIG. 1, a hydraulic shovel as one example of a construction machine comprises an upper frame 1, a cabin 2 provided on the upper frame 1, an engine 3, a fuel tank 4, a cooling fan 5, a hydraulic pump 6, and a detection device (fuel property detection device: see FIG. 2) 24 for detecting a property (physical property such as kinetic viscosity or density, or chemical property) of fuel to be supplied from the fuel tank 4 to the engine 3.

The engine 3 is disposed rearward of the cabin 2 in a posture where a longitudinal direction of the engine 3 is oriented in a right-left direction. The fuel tank 4 is disposed on a right side of the cabin 2, and capable of storing a predetermined amount of fuel. The cooling fan 5 is disposed on a left side of the engine 3, and adapted to be driven by a drive power of the engine 3. The hydraulic pump 6 is disposed on a right side of the engine 3, and adapted to be driven by the drive power of the engine 3.

Figure 2:
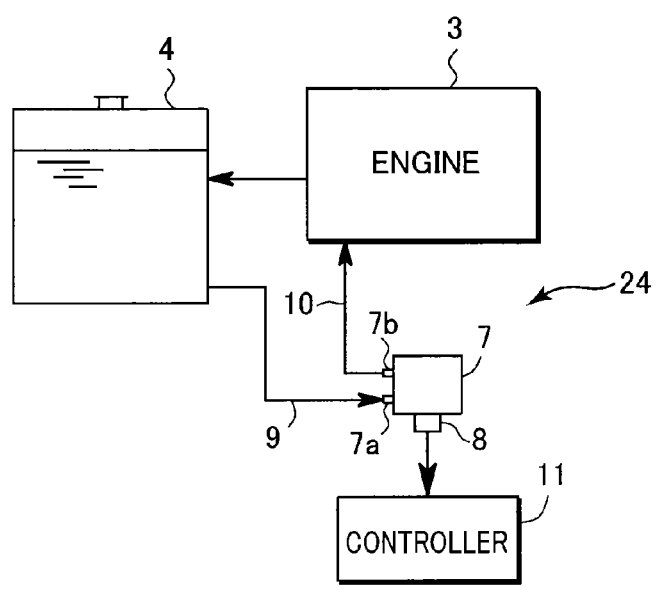
FIG. 2 is a layout diagram of devices in the hydraulic shovel illustrated in FIG. 1.

As illustrated in FIG. 2, the detection device 24 comprises an inlet pipe (a part of a fuel supply pipe line) 9 connected to the fuel tank 4, an outlet pipe (a part of the fuel supply pipe line) 10 connected to the engine 3, a sub-tank 7 connected to the inlet pipe 9 and the outlet pipe 10, a sensor 8 provided to the sub-tank 7, and a controller 11 electrically connected to the sensor 8.

Figure 3:
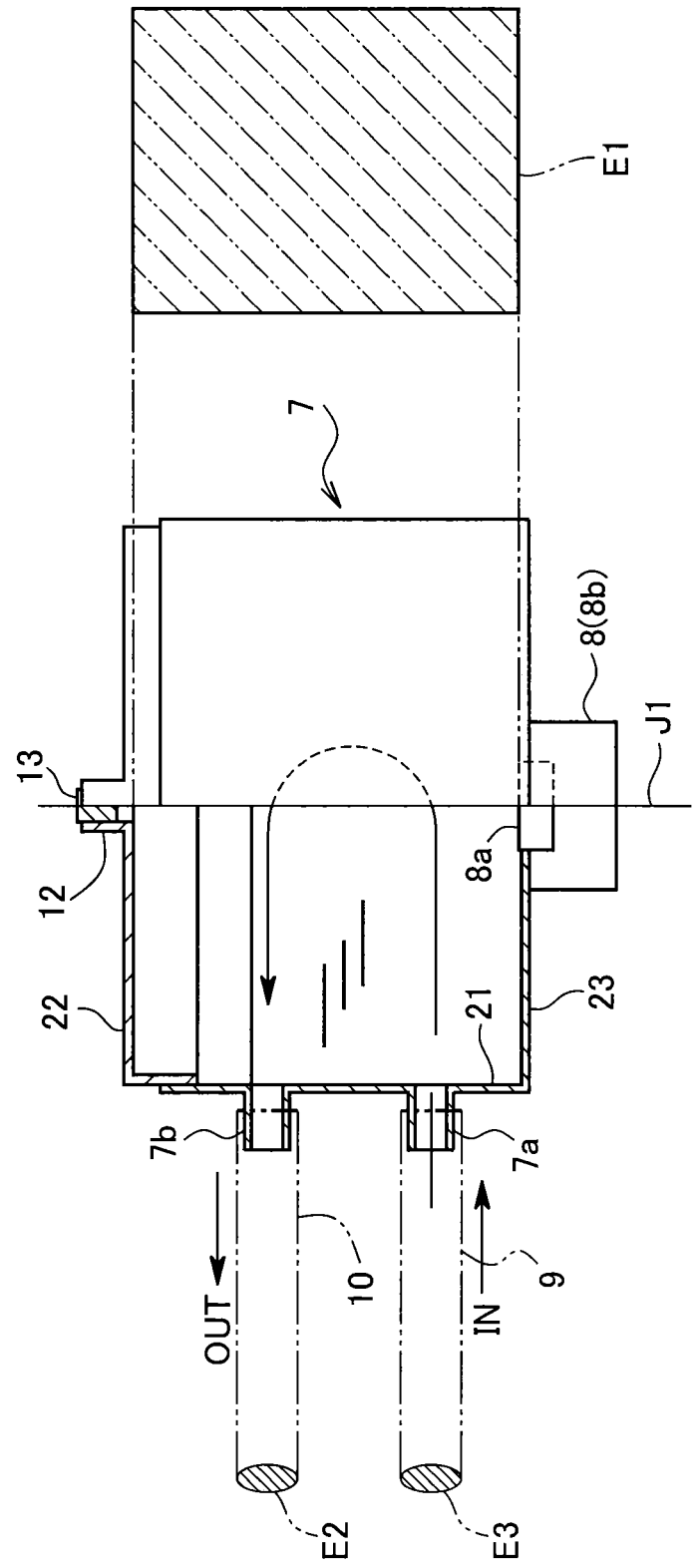
FIG. 3 is a half sectional front view of a sub-tank illustrated in FIG. 1.

The sub-tank 7 is provided in the course of a fuel supply pipe line for supplying therethrough fuel from the fuel tank 4 to the engine 3 (between the inlet pipe 9 and the outlet pipe 10). Specifically, the sub-tank 7 is capable of storing fuel by a given amount less than that (capacity) in the fuel tank 4. Further, as illustrated in FIG. 3, a flow passage cross-sectional area E1 of the sub-tank 7 perpendicular to a fuel flow direction is greater than each of a flow passage cross-sectional area E2 of the outlet pipe 10 perpendicular to the fuel flow direction, and a flow passage cross-sectional area E3 of the inlet pipe 9 perpendicular to the fuel flow direction. Thus, a flow velocity of fuel introduced into the sub-tank 7 becomes lower than a flow velocity of fuel in each of the pipes 9, 10, so that a flow quantity of the fuel introduced into the sub-tank 7 is stabilized. A property of the fuel reduced in flow velocity and stabilized in flow quantity in the above manner is detected by the sensor 8.

As enlargedly illustrated in FIGS. 3 and 4, the sub-tank 7 has: a sidewall 21 formed over the entire circumference around an axis J1 extending along an up-down direction; a top wall 22 closing an upper opening of the sidewall 21; a bottom wall 23 closing a lower opening of the sidewall 21; a fuel inlet 7a and a fuel outlet 7b each formed in the sidewall 21; an air-releasing air vent port 12 formed in the top wall 22; and a plug 13 attachable and detachable with respect to the air vent port 12. The fuel inlet 7a is connected to the inlet pipe 9. The fuel outlet 7b is connected to the outlet pipe 10.

The sidewall 21 has a cylindrical shape with the axis J1 as a central axis. The sidewall 21 is formed with the fuel inlet 7a and the fuel outlet 7b in such a manner that they are arranged one above the other in side-by-side relation at approximately same positions in a circumferential direction about the axis J1. In other words, the fuel inlet 7a and the fuel outlet 7b are arranged one above the other in side-by-side relation on the same plane P1 (see FIG. 4) along the up-down direction. Specifically, the fuel inlet 7a protrudes horizontally from a lower portion of the sidewall 21, and the fuel outlet 7b protrudes horizontally from an upper portion of the sidewall 21 at a position approximately just above the fuel inlet 7a. That is, the fuel inlet 7a and the fuel outlet 7b are arranged one above the other in side-by-side relation at approximately same positions in the circumferential direction of the sidewall 21, while extending parallel to each other.

The sensor 8 is operable to detect the property of fuel within the sub-tank 7, and transmit a resulting detection signal to the controller 11 described later. More specifically, the sensor 8 comprises a sensing section 8a capable of detecting a property of fuel, and a support section 8b for supporting the sensing section 8a. The support section 8b is fixed to the bottom wall 23 of the sub-tank 7 under a condition that the sensing section 8a is exposed to an inside of the sub-tank 7 through a hole formed in the bottom wall 23. For example, the sensing section 8a is configured to detect a kinetic viscosity of fuel through contact with the fuel.

The sensor 8 (sensing section 8a) is disposed on the plane P1 (see FIG. 4) including respective axes of the pipes 9, 10. In other words, the sensor 8 and the pipes 9, 10 are arranged on the same plane P1 along the up-down direction. More specifically, the sensor 8 in the first embodiment is provided in a central portion of the bottom wall 23 of the sub-tank 7. Thus, the sensor 8 can reliably detect the property of fuel during a course after being introduced from the inlet pipe 9 through until it reaches the outlet pipe 10.

Although the sensor 8 in the first embodiment is provided in the central portion of the bottom wall 23 of the sub-tank 7, the present invention is not limited thereto. For example, in a situation where another structural element, such as a drain port, is provided in the central region of the bottom wall 23 of the sub-tank 7, the sensor 8 may be provided at a position offset from a center of the bottom wall 23 of the sub-tank 7 so as to prevent interference with the structural element.

The controller 11 is electrically connected to the sensor 8, and operable, in response to receiving a detection signal from the sensor 8, to perform processing for determination, indication and alarm on adequacy of fuel.

The air vent hole 12 is provided in a central portion of the top wall 22 of the sub-tank 7. The plug 13 is adapted to close the air vent port 12 under a condition that it is attached to the air vent port 12.

As described above, in the detection device 24, the sub-tank 7 with the flow passage cross-sectional area E1 greater than each of the flow passage cross-sectional areas E3, E2 of the pipes 9, 10 is provided in the course of the fuel supply pipeline, so that it becomes possible to reduce a fuel flow velocity within the sub-tank 7 and stabilize a flow quantity within the sub-tank 7.

In addition, the detection device 24 has the sensor 8 capable of detecting the property of fuel reduced in flow velocity and stabilized in flow quantity in the above manner, so that it becomes possible to ensure a time required for the sensor 8 to detect the fuel property, and stabilize the fuel flow quantity, as a fundamental effect.

Furthermore, the detection device 24 has high layout flexibility during mounting on the hydraulic shovel (upper frame 1) for the following two reasons.

(I) It can be installed by freely selecting an arbitrary position advantageous in avoiding interference with other device, in a space between the fuel tank 4 and the engine 3 (in the embodiment illustrated in FIG. 1, a rear end region of the upper frame 1 on the right side of the engine 3 (a region rearward of the hydraulic pump 6)).

(II) A volume of the sub-tank can be set to a minimum value for allowing the fuel flow velocity to be reduced to a value required for the fuel property detection, so that the sub-tank can be downsized.

That is, the detection device 24 can be added on to an existing construction machine (in the first embodiment, the hydraulic shovel) and is capable of employing an in-pipeline detection system having high layout flexibility, while enhancing accuracy and stability of the fuel property detection.

In addition to the above fundamental effect, the detection device 24 according to the first embodiment can obtain the following functions/effects.

(i) In the detection device 24, the fuel inlet 7a of the sub-tank 7 is disposed at a position closer to the sensor 8 than the fuel outlet 7b, so that fuel flows into the sub-tank 7 from a position closer to the sensor 8, which makes it possible to quickly detect a change (switching) from adequate fuel to inadequate fuel or vice versa.

(ii) In the detection device 24, the fuel inlet 7a is disposed below the fuel outlet 7b, so that fuel flows into the sub-tank 7 from a relatively lower position, and, after flowing upwardly, flows out from a relatively upper position, which makes it possible to increase a speed itself of the fuel-type switching within the fuel tank 7, as compared to cases where the fuel inlet 7a and the fuel outlet 7b are arranged at the same position in the up-down direction, and more quickly detect the switching.

(iii) In the detection device 24, the fuel inlet 7a and the fuel outlet 7b are arranged one above the other in side-by-side relation at approximately same positions about the up-down axis J1, so that a curved flow is formed in which fuel U-turns upwardly from the bottom side within the sub-tank 7 and flows out, as illustrated in FIG. 3. The curved flow allows the fuel flow within the sub-tank 7 to become slower, which makes it possible to further enhance the accuracy and stability of the property detection.

(iv) The fuel flow becomes sufficiently slow by the curved flow, which eliminates a need for enlarging the sub-tank 7, aiming for reducing the fuel flow velocity. This makes it possible to further downsize the sub-tank 7, and provide higher layout flexibility during mounting of the detection device 24 to the hydraulic shovel.

The sensor 8 may be installed at a position just below a turn-around point of the U-shaped curved flow or therearound. In this case, a lowest part of the fuel in terms of the flow velocity is detected by the sensor, which provides further enhanced accuracy of the property detection.

(v) In the detection device 24, the sensor 8 is disposed on the plane P1 including the axis of the fuel inlet 7a and the axis of the fuel inlet 7b, so that it becomes possible to reliably detect the property of fuel during a course after being introduced from the fuel inlet 7a through until it reaches the fuel outlet 7b.

(vi) In the detection device 24, the flow passage cross-sectional area E1 of the sub-tank 7 is greater than each of the flow passage cross-sectional areas E3, E2 of the inlet pipe 9 and the outlet pipe 10, so that it becomes possible to reliably reduce the flow velocity of fuel introduced from the inlet pipe 9 into the sub-tank 7. Thus, the accuracy of the fuel property detection can be further improved.

FIGS. 5 to 9 are graphs illustrating respective schematic configurations of detection devices according to the first embodiment and second to fifth embodiments of the present invention, and respective detection performance test results of the detection devices.

Conditions and method for the detection performance test are as follows. A shape and a volume of the sub-tank 7 are the same for all of the embodiments. Fuel flowing through the sub-tank 7 is changed (switched) from light oil to kerosene at a predetermined timing. A good or bad evaluation on a test result is performed based on how an output value (discrimination value) has changed over time. A timing of fuel-type switching is indicated at a left end in each of FIGS. 5B, 6B, 7B, 8B and 9B.

A flow quantity and a flow velocity of fuel to be supplied are the same for all of the embodiments. A fuel temperature within the sub-tank 7 is changed by exogenous influences. Thus, in FIGS. 5B, 6B, 7B, 8B and 9B, a discrimination value converted as a value at a fuel temperature of 30° C. is indicated.

Figure 5A:
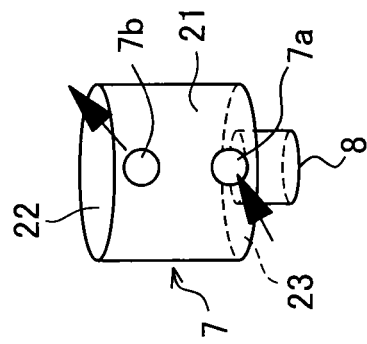
FIG. 5A is a diagram schematically illustrating the detection device according to the first embodiment of the present invention.
Figure 5B:
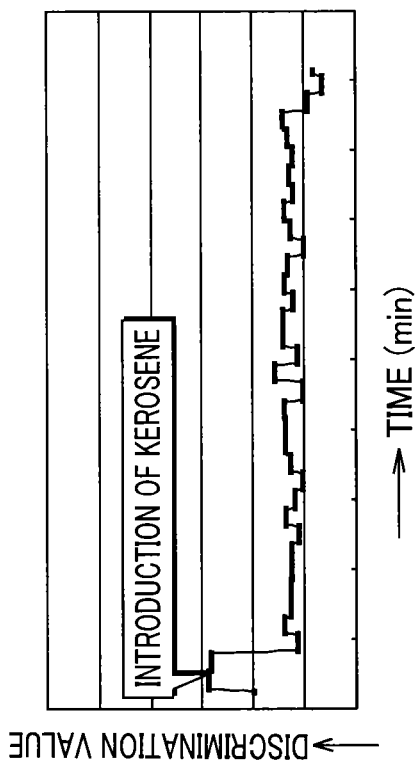
FIG. 5B is a graph illustrating a detection performance test result of the detection device.

As illustrated in FIG. 5B, in the first embodiment, the discrimination value was changed within a short period of time (2 to 3 minutes) after the fuel-type switching, and subsequently maintained at an approximately constant value.

In other words, the detection device 24 according to the first embodiment could quickly detect the fuel-type switching and obtain stable detection performance. It would be considered that the reason for this result is as follows.

In the detection device 24, the fuel inlet 7a and the fuel outlet 7b are arranged one above the other in side-by-side relation at approximately same positions about the up-down axis J1, and the sensor 8 is provided just below a turn-around region of the curved flow (see FIG. 3) between the fuel inlet 7a and the fuel outlet 7b. Thus, according to the curved flow, fuel flows upwardly from the bottom side within the sub-tank 7, so that two types of fuels are stirred and quickly mixed together, and an oil property within the sub-tank 7 is quickly changed due to the mixing. Then, the change in oil property within the sub-tank 7 is captured by the sensor 8 quickly and accurately, so that it becomes possible to quickly detect the fuel-type switching and obtain stable detection performance.

As illustrated in FIG. 6A, in a detection device according to the second embodiment, the fuel inlet 7a is provided at a position slightly upward of an intermediate position of the sidewall 21 of the sub-tank 7. On the other hand, in the detection device according to the second embodiment, the fuel outlet 7b is provided in the top wall 22 of the sub-tank 7. A position of the sensor 8 in each of the second to fifth embodiments is the same as that of the sensor 8 in the first embodiment.

As illustrated in FIG. 6B, in the detection device according to the second embodiment, although the fuel-type switching can be quickly detected, stability in the discrimination value is inferior to the first embodiment. It would be considered that the reason for this result is as follows.

In the detection device according to the second embodiment, the fuel inlet 7a is provided in the sidewall 21 of the sub-tank 7, and the fuel outlet 7b is provided in the top wall 22 of the sub-tank 7, so that a fuel flow within the sub-tank 7 is changed from a horizontal direction to an upward direction during a course between the fuel inlet 7a and the fuel outlet 7b. Thus, a flow around the sensor 8 is likely to be disturbed by both influences of a fuel flow introduced from the fuel inlet 7a and a fuel flow toward the fuel outlet 7b, and stability in the discrimination value becomes deteriorated due to the disturbed flow or turbulence.

Figure 7B:
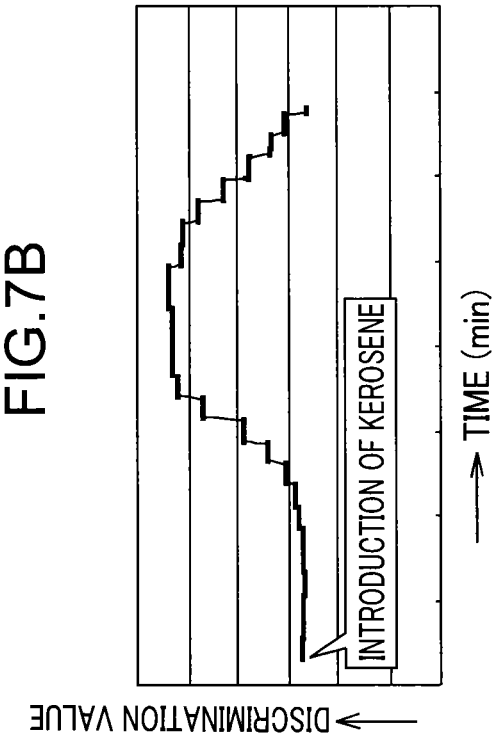
FIG. 7B is a graph illustrating a detection performance test result of the detection device.
Figure 7A:
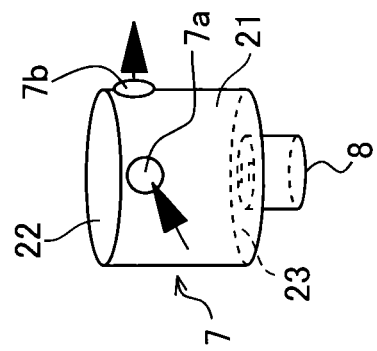
FIG. 7A is a diagram schematically illustrating a detection device according to a third embodiment of the present invention.

As illustrated in FIG. 7A, in a detection device according to the third embodiment, the fuel inlet 7a and the fuel outlet 7b are provided in an upper portion of the sidewall 21 of the sub-tank 7. More specifically, the fuel inlet 7a and the fuel outlet 7b are disposed at positions having approximately the same height and offset about the axis J1 by 90 degrees.

As illustrated in FIG. 7B, in the detection device according to the third embodiment, a time required until detection of the fuel-type switching becomes longer, as compared to the first and second embodiments. It would be considered that the reason for this result is as follows.

In the detection device according to the third embodiment, both of the fuel inlet 7a and the fuel outlet 7b are disposed at upper positions of the sub-tank 7, so that a liquid interface is formed in an upper region of the inside of the sub-tank 7. Due to the formation of the liquid interface, fuel introduced into the sub-tank 7 slowly flows in the upper region of the inside of the sub-tank 7 in a circular motion, so that mixing in the up-down direction is less likely to occur, which causes an increase in time required until detection of the fuel-type switching.

Figure 8A:
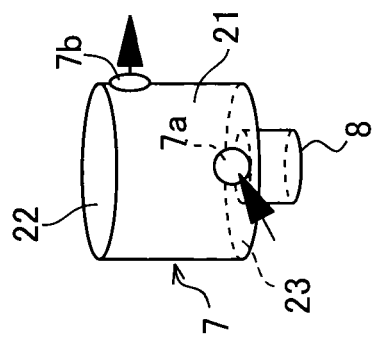
FIG. 8A is a diagram schematically illustrating a detection device according to a fourth embodiment of the present invention.

As illustrated in FIG. 8A, in a detection device according to the fourth embodiment, the fuel inlet 7a is provided in a lower portion of the sidewall 21 of the sub-tank 7, and the fuel outlet 7b is provided in an upper portion of the sidewall 21 of the sub-tank 7. The fuel outlet 7b is disposed at a position offset from the fuel outlet 7b about the axis J1 by 90 degrees.

Figure 8B:
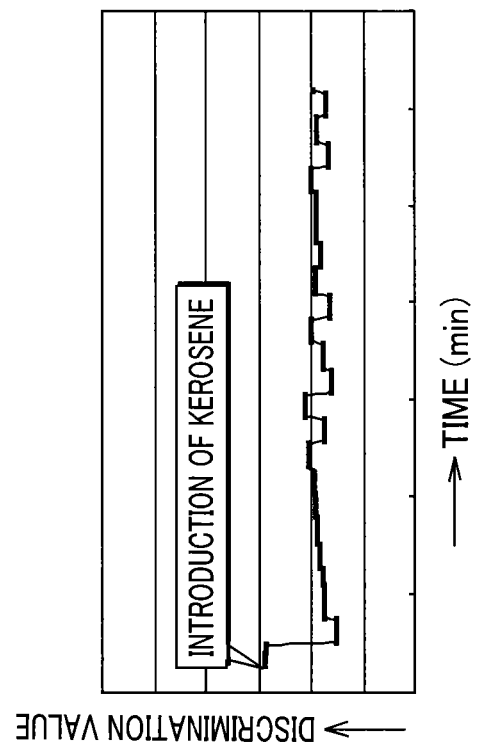
FIG. 8B is a graph illustrating a detection performance test result of the detection device.

As illustrated in FIG. 8B, in the detection device according to the fourth embodiment, although the fuel-type switching can be quickly detected, the output of the discrimination value lacks stability. It would be considered that the reason for this result is as follows.

In the detection device according to the fourth embodiment, the fuel inlet 7a and the fuel outlet 7b are positionally offset from each other in the up-down direction and further positionally offset from each other about the axis J1 by 90 degrees, so that a flow occurs in which fuel introduced into the sub-tank 7 moves from the fuel inlet 7a upwardly while being twisted toward the fuel outlet 7b. Due to influence of this flow, the output of the discrimination value lacks stability.

Figure 9A:
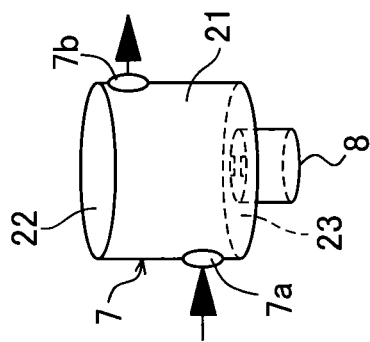
FIG. 9A is a diagram schematically illustrating a detection device according to a fifth embodiment of the present invention.

As illustrated in FIG. 9A, in a detection device according to the fifth embodiment, the fuel inlet 7a is provided in a lower portion of the sidewall 21 of the sub-tank 7, and the fuel outlet 7b is provided in an upper portion of the sidewall 21 of the sub-tank 7. Further, the fuel inlet 7a and the fuel outlet 7b are disposed positionally offset from each other about the axis J1 by 180 degrees.

Figure 9B:
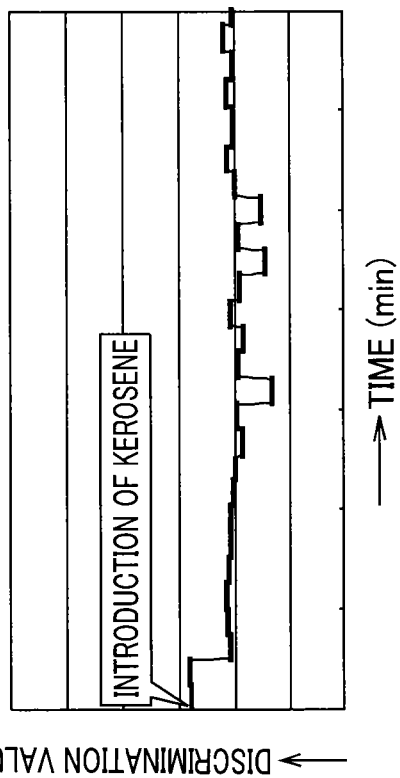
FIG. 9B is a graph illustrating a detection performance test result of the detection device.

As illustrated in FIG. 9B, in the detection device according to the fifth embodiment, although the fuel-type switching can be detected within a relatively short period of time, the output of the discrimination value lacks stability. It would be considered that the reason for this result is as follows.

In the detection device according to the fifth embodiment, the fuel inlet 7a and the fuel outlet 7b are positionally offset from each other in the up-down direction and further positionally offset from each other about the axis J1 by 180 degrees, so that a flow occurs in which fuel introduced into the sub-tank 7 moves from the fuel inlet 7a upwardly toward the fuel outlet 7b. Due to influence of this flow, the output of the discrimination value lacks stability.

Considering all the above results together, among the first to fifth embodiments, the detection device according to the first embodiment is the most excellent in detection performance. This, it can be concluded that the first embodiment is the best mode among the first to fifth embodiments.

(Other Embodiments)

Figure 10:
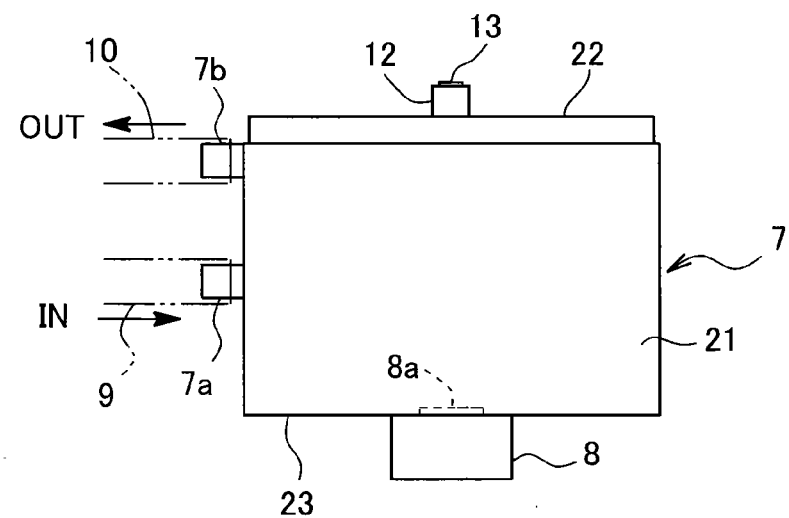
FIG. 10 is a front view illustrating a detection device according to another embodiment of the present invention.
Figure 11:
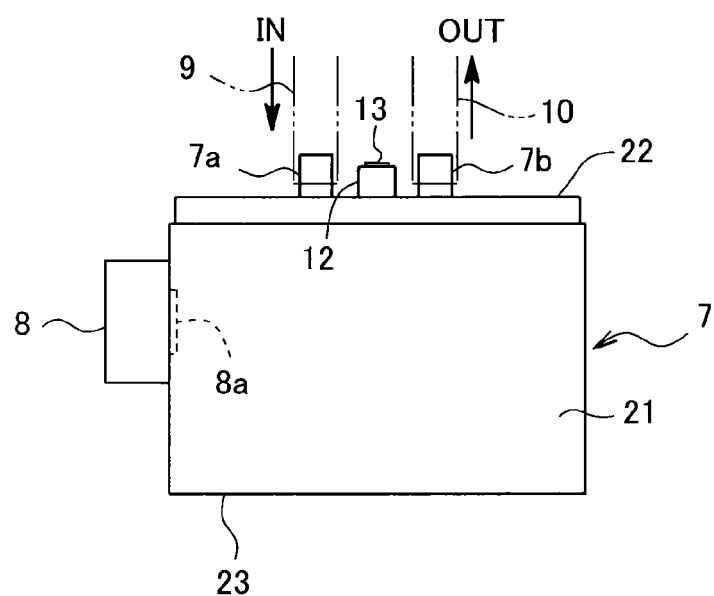
FIG. 11 is a front view illustrating a detection device according to yet another embodiment of the present invention.

(1) FIG. 10 illustrates a detection device according to a sixth embodiment. FIG. 11 illustrated a detection device according to a seventh embodiment. In the detection device illustrated in FIG. 10, the fuel outlet 7b is provided in an uppermost portion of the sub-tank 7. In the detection device illustrated in FIG. 11, both of the fuel inlet 7a and the fuel outlet 7b are provided in the uppermost portion of the sub-tank 7. More specifically, in the detection device illustrated in FIG. 10, the fuel outlet 7b is provided in an uppermost portion of the sidewall 21 of the sub-tank 7. In the detection device illustrated in FIG. 11, both of the fuel inlet 7a and the fuel outlet 7b are provided in the top wall 22 of the sub-tank 7.

In the detection device according to the sixth embodiment, at least the fuel outlet 7b is provided in the uppermost portion of the sub-tank 7, so that air in fuel is led out from the sub-tank 7 through the fuel outlet 7b together with fuel without staying in the sub-tank 7. Thus, in the detection device according to the sixth embodiment, it becomes possible to eliminate a need for an air releasing operation of detaching the air vent plug 13 to open the air vent port 12, or it is only necessary to minimumly perform the operation.

Specifically, in order to simplify the air releasing operation, it is necessary that the fuel outlet 7b is provided in the uppermost portion of the sidewall 21 of the sub-tank 7 (FIG. 10), or in the uppermost portion (top wall 22: FIG. 11) in the entire sub-tank 7.

In the detection device illustrated in FIG. 11, the sensor 8 is provided to the side wall 21 of the sub-tank 7. Thus, a curved flow in which fuel introduced from the fuel inlet 7a U-turns and returns to the fuel outlet 7b is generated within the sub-tank 7, and the fuel property is reliably detected by the sensor 8 in the course of the curved flow. Preferably, in the detection device illustrated in FIG. 11, the sensor 8 is provided at a position on a lateral side of a turn-around point of the U-shaped curved flow, to the same effect as that in the first embodiment. Further, in the detection device illustrated in FIG. 11, it is preferable that the sensor 8 (sensing section 8a) is disposed on a plane including respective axes of the fuel inlet 7a and the fuel outlet 7b, to the same effect as that in the first embodiment.

(2) In the above embodiments, the sub-tank 7 is installed in a posture where the cylindrical-shaped sidewall 21 is disposed about the axis J1 extending along the up-down direction. Alternatively, as in a detection device according to an eighth embodiment illustrated in FIG. 12, the sub-tank 7 may be installed in a posture where the sidewall 21 is disposed about an axis extending along a horizontal direction. Specifically, a laterally-oriented portion of the sidewall 21, the top wall 22 and the bottom wall 23 make up a sidewall in the eighth embodiment. Further, an upwardly-oriented portion of the sidewall 21 makes up a top wall in the eighth embodiment, and a downwardly-oriented portion of the sidewall 21 makes up a bottom wall in the eighth embodiment.

Figure 12:
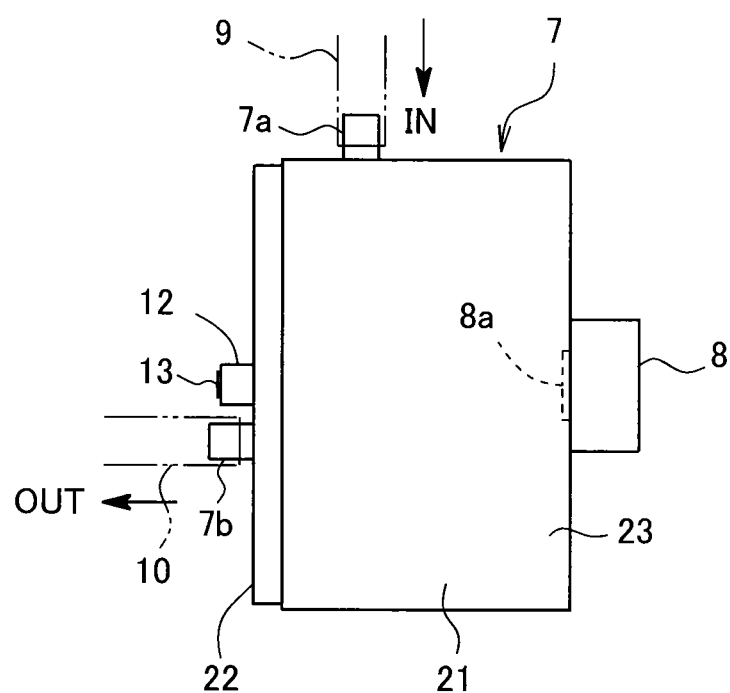
FIG. 12 is a front view illustrating a detection device according to still another embodiment of the present invention.

In this case, an arrangement of the fuel inlet 7a, the fuel outlet 7b and the sensor 8 is not limited to that illustrated in FIG. 12, but any other suitable arrangement may be selected.

The detection device having the sub-tank 7 horizontally disposed as illustrated in FIG. 12 can also obtain the fundamental function/effect of being able to employ the in-pipeline detection system while improving accuracy and stability of the fuel property detection, as with the first to seventh embodiments.

The above specific embodiments primarily include an invention having the following features.

A fuel property detection device according to the above embodiments is designed to detect a property of fuel to be supplied to an engine from a fuel tank for storing fuel. The fuel property detection device comprises: a sub-tank provided in the course of a fuel supply pipeline connecting the engine and the fuel tank, and capable of storing a given amount of fuel; and a sensor provided to the sub-tank and capable of detecting the property of fuel within the sub-tank, wherein the sub-tank has a fuel inlet for introducing therethrough fuel from the fuel tank, and a fuel outlet for sending out therethrough the fuel toward the engine.

In the fuel property detection device according to the above embodiments, the sub-tank capable of storing a given amount of fuel is provided in the course of the fuel supply pipeline, so that it becomes possible to reduce a fuel flow velocity within the sub-tank and stabilize a fuel flow quantity within the sub-tank. In addition, the fuel property detection device according to the above embodiments is provided with the sensor capable of detecting the property of fuel within the sub-tank, so that it becomes possible to ensure a time required for the detection by the sensor, and stabilize the fuel flow quantity.

Furthermore, the sub-tank has high layout flexibility during mounting on a construction machine for the following two reasons.

(I) It can be installed by freely selecting an arbitrary position advantageous in avoiding interference with other device, in a space between the fuel tank and the engine.

(II) A volume of the sub-tank can be set to a minimum value for allowing the fuel flow velocity to be reduced to a value required for the fuel property detection, so that the sub-tank can be downsized.

That is, the detection device can be added on to an existing construction machine and is capable of employing an in-pipeline detection system having high layout flexibility, while enhancing accuracy and stability of the fuel property detection.

The term "property of fuel" means a physical property such as kinetic viscosity or density, or a chemical property of fuel.

Preferably, in the fuel property detection device, the fuel inlet of the sub-tank is disposed at a position closer to the sensor than the fuel outlet.

In this fuel property detection device, the fuel inlet of the sub-tank is disposed at a position closer to the sensor than the fuel outlet, so that fuel flows into the sub-tank from a position closer to the sensor, which makes it possible to quickly detect a change from adequate fuel to inadequate fuel or vice versa.

Preferably, in the fuel property detection device, the fuel inlet is disposed below the fuel outlet.

In this fuel property detection device, the fuel inlet is disposed below the fuel outlet, so that fuel flows into the sub-tank from a relatively lower position, and, after flowing upwardly, flows out from a relatively upper position, which makes it possible to increase a speed itself of the fuel switching within the fuel tank, as compared to cases where the fuel inlet and the fuel outlet are arranged at the same position in the up-down direction, and more quickly detect the switching.

Preferably, the fuel inlet is capable of introducing fuel to the sub-tank in a lateral direction, and the fuel outlet is capable of leading fuel out of the sub-tank in a lateral direction, wherein the fuel inlet and the fuel outlet of the sub-tank are arranged one above the other in side-by-side relation on the same plane along an up-down direction.

In this fuel property detection device, the fuel inlet capable of introducing fuel to the sub-tank in a lateral direction and the fuel outlet capable of leading fuel out of the sub-tank in a lateral direction are arranged one above the other in side-by-side relation on the plane along the up-down direction, so that a curved flow is formed in which fuel U-turns upwardly from the bottom side within the sub-tank and flows out.

The curved flow allows the fuel flow within the sub-tank to become slower, which makes it possible to further enhance the accuracy and stability of the fuel property detection.

The fuel flow becomes slow by the curved flow, which eliminates a need for enlarging the sub-tank, aiming for reducing the fuel flow velocity. This makes it possible to further downsize the sub-tank, and provide higher layout flexibility during mounting of the detection device to a construction machine.

Preferably, in the fuel property detection device, the fuel outlet of the sub-tank is disposed in an uppermost portion of the sub-tank.

In this fuel property detection device, the fuel outlet of the sub-tank is disposed in an uppermost portion of the sub-tank, so that air in fuel is led out from the sub-tank together with fuel without staying in the sub-tank. Thus, it becomes possible to eliminate a need for an operation for releasing air from the sub-tank, or it is only necessary to minimumly perform the operation.

Specifically, as the sub-tank, it is possible to employ a tank which has a sidewall formed over an entire circumference about an axis along an up-down direction, a top wall closing an upper opening of the sidewall, and a bottom wall closing a lower opening of the sidewall.

Preferably, in the above fuel property detection device, the sensor is provided to the bottom wall of the sub-tank, and the fuel inlet and fuel outlet are provided in the sidewall of the sub-tank, wherein the fuel inlet is disposed below the fuel outlet.

In this fuel property detection device, the sensor is provided to the bottom wall of the sub-tank, and the fuel inlet is disposed below the fuel outlet, so that fuel flows into the sub-tank from a position closer to the sensor, which makes it possible to quickly detect a change from adequate fuel to inadequate fuel or vice versa.

Preferably, in the fuel property detection device, the fuel inlet and fuel outlet of the sub-tank are arranged one above the other in side-by-side relation at approximately same positions in a circumferential direction of the sidewall.

In this fuel property detection device, the fuel inlet and fuel outlet are arranged one above the other in side-by-side relation at approximately same positions about an axis along the up-down direction, so that a curved flow is formed in which fuel U-turns upwardly from the bottom side within the sub-tank and flows out. The curved flow allows the fuel flow within the sub-tank to become slower, which makes it possible to further enhance the accuracy and stability of the property detection. The fuel flow becomes slow by the curved flow, which eliminates a need for enlarging the sub-tank, aiming for reducing the fuel flow velocity. This makes it possible to further downsize the sub-tank, and provide higher layout flexibility during mounting of the detection device to a construction machine.

Preferably, in the fuel property detection device, the sensor is provided to the bottom wall of the sub-tank, the fuel inlet is provided in the sidewall of the sub-tank, and fuel outlet is provided in the top wall of the sub-tank.

In this fuel property detection device, the fuel outlet of the sub-tank is provided in the top wall of the sub-tank, so that air in fuel is led out from the sub-tank together with fuel without staying in the sub-tank. Thus, it becomes possible to eliminate a need for an operation for releasing air from the sub-tank, or it is only necessary to minimumly perform the operation.

Preferably, in the fuel property detection device, the sensor, the fuel inlet and the fuel outlet are arranged on the same plane.

In this fuel property detection device, the sensor, the fuel inlet and the fuel outlet are arranged on the same plane, so that it becomes possible to reliably detect the property of fuel during a course after being introduced from the fuel inlet pipe through until it reaches the fuel outlet.

Preferably, in the fuel property detection device, the fuel property detection device comprises an inlet pipe connected to the fuel inlet of the sub-tank and connectable to the fuel tank, and an outlet pipe connected to the fuel outlet of the sub-tank and connectable to the engine, wherein a flow passage cross-sectional area of the sub-tank perpendicular to a flow direction of the fuel is greater than each of respective flow passage cross-sectional areas of the inlet pipe and the outlet pipe.

In this fuel property detection device, the flow passage cross-sectional area of the sub-tank is greater than each of the flow passage cross-sectional areas of the inlet pipe and the outlet pipe, so that it becomes possible to reliably reduce the flow velocity of fuel introduced from the inlet pipe into the sub-tank. Thus, the accuracy of the fuel property detection can be further improved.

Further, a construction machine according to the above embodiments comprises: the above fuel property detection device; a fuel tank connected to the inlet pipe of the fuel property detection device; and an engine connected to the outlet pipe of the fuel property detection device.

The construction machine according to the above embodiments comprises the above fuel property detection device, so that it becomes possible to employ the in-pipeline detection system while enhancing accuracy and stability of the fuel property detection.

INDUSTRIAL APPLICABILITY

The present invention makes it possible to employ the in-pipeline detection system while improving accuracy and stability of the fuel property detection.

EXPLANATION OF CODES

E1 to E3: flow passage cross-sectional area
J1: axis along up-down direction
P1: plane including axis of fuel inlet and axis of fuel outlet
3: engine
4: fuel tank
7: sub-tank
7a: fuel inlet
7b: fuel outlet
8: sensor
9: inlet pipe (part of fuel supply pipeline)
10: outlet pipe (part of fuel supply pipeline)
21: sidewall
22: top wall
23: bottom wall
24: detection device

What is claimed is:

1. A fuel property detection device for a construction machine, which is designed to detect a property of fuel to be supplied to an engine from a fuel tank for storing fuel, comprising:

a sub-tank provided in the course of a fuel supply pipeline connecting the engine and the fuel tank, and capable of storing a given amount of fuel; and a sensor provided to the sub-tank and capable of detecting the property of fuel within the sub-tank, wherein the sub-tank has a fuel inlet for introducing therethrough fuel from the fuel tank, and a fuel outlet for sending out therethrough the fuel toward the engine, wherein the sub-tank has a sidewall formed over an entire circumference about an axis along an up-down direction, wherein the fuel inlet and fuel outlet of the sub-tank are provided in the sidewall of the sub-tank at approximately the same position in the circumferential direction of the sidewall and in such a manner that the fuel inlet is disposed below the fuel outlet, and wherein the sensor is provided to a lower portion of the sub-tank.

2. The fuel property detection device for a construction machine according to claim 1, wherein the fuel inlet of the sub-tank is disposed at a position closer to the sensor than the fuel outlet.

3. The fuel property detection device for a construction machine according to claim 1, wherein the fuel inlet is capable of introducing fuel to the sub-tank in a lateral direction, and the fuel outlet is capable of leading fuel out of the sub-tank in a lateral direction, and wherein the fuel inlet and the fuel outlet of the sub-tank are arranged one above the other in side-by-side relation on a same plane along an up-down direction.

4. The fuel property detection device for a construction machine according to claim 1, wherein the fuel outlet of the sub-tank is disposed in an uppermost portion of the sidewall of the sub-tank.

5. The fuel property detection device for a construction machine according to claim 1, wherein the sub-tank has a top wall closing an upper opening of the sidewall, and a bottom wall closing a lower opening of the sidewall.

6. The fuel property detection device for a construction machine according to claim 1, wherein the sensor is provided to the bottom wall of the sub-tank.

7. The fuel property detection device for a construction machine according to claim 1, wherein the sensor, the fuel inlet and the fuel outlet are arranged on a same plane.

8. The fuel property detection device for a construction machine according to claim 1, further comprising an inlet pipe connected to the fuel inlet of the sub-tank and connectable to the fuel tank, and an outlet pipe connected to the fuel outlet of the sub-tank and connectable to the engine, and wherein a flow passage cross-sectional area of the sub-tank perpendicular to a flow direction of the fuel is greater than each of respective flow passage cross-sectional areas of the inlet pipe and the outlet pipe.

9. A construction machine comprising:

the fuel property detection device for a construction machine according to claim 8;

a fuel tank connected to the inlet pipe of the fuel property detection device; and an engine connected to the outlet pipe of the fuel property detection device.

* * * * *